United States Patent [19]

Bonis

[11] Patent Number: 5,391,148
[45] Date of Patent: Feb. 21, 1995

[54] RUPTURABLE BALLOON SAFETY CATHETER

[76] Inventor: Peter Bonis, 2 Clarendon St. #408, Boston, Mass. 02116

[21] Appl. No.: 726,908

[22] Filed: Jul. 8, 1991

[51] Int. Cl.⁶ .............................................. A61M 25/00
[52] U.S. Cl. ...................................... 604/96; 604/264; 604/280; 606/192
[58] Field of Search ................. 604/96, 101, 246, 280, 604/284; 606/191–194; 128/207.14

[56]  References Cited

U.S. PATENT DOCUMENTS

| | | | |
|---|---|---|---|
| 3,951,153 | 4/1976 | Leuccci | 604/54 |
| 4,811,737 | 3/1989 | Rydell | 604/96 |
| 4,932,956 | 6/1990 | Reddy et al. | 604/101 |
| 5,078,681 | 1/1992 | Kawashima | 604/96 |
| 5,085,635 | 2/1992 | Cragg | 604/96 |
| 5,102,416 | 4/1992 | Rock | 606/194 |

*Primary Examiner*—C. Fred Rosenbaum
*Assistant Examiner*—Chalin Smith
*Attorney, Agent, or Firm*—George E. Kersey

[57] ABSTRACT

An improved balloon catheter is disclosed that facilitates catheter release when a pull is entered upon the inserted catheter while the balloon is inflated in a body passageway. The catheter is provided with one or more weakened regions on the inflatable balloon portion. These weakened regions may be provided by portions of non-uniform thicknesses arranged circumferentially around the balloon. These weakened regions rupture and release the inflation when the catheter is pulled from its inserted, inflated position. This mechanism allows for a tight seal on the body passageway while alleviating the danger of accidental removal with the balloon in its inflated state.

17 Claims, 4 Drawing Sheets

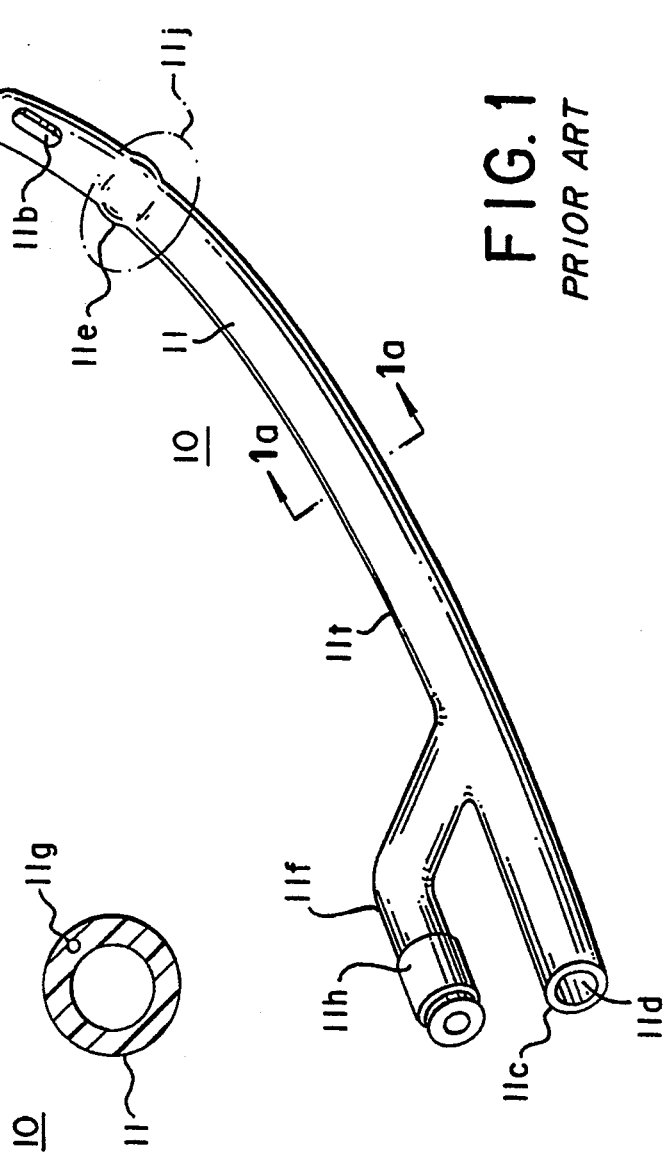

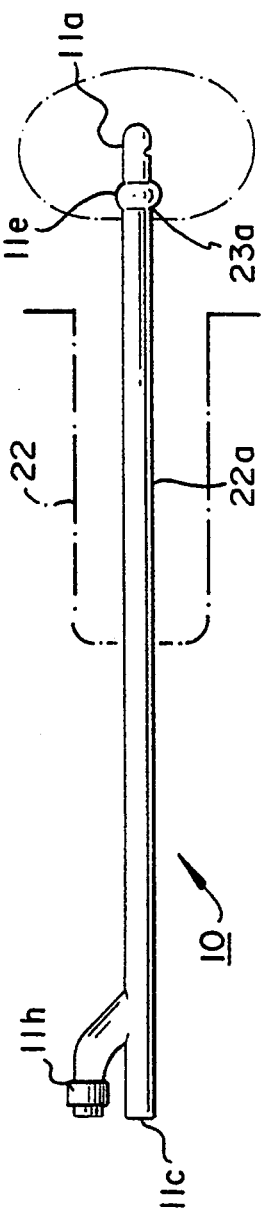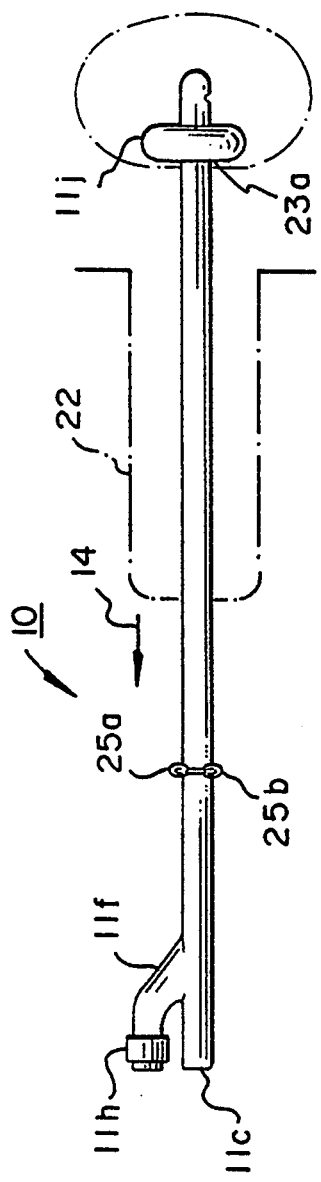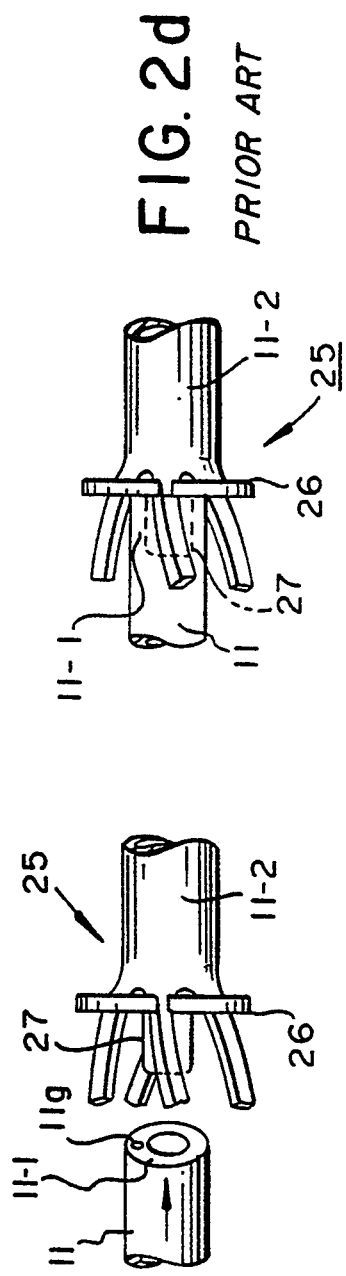

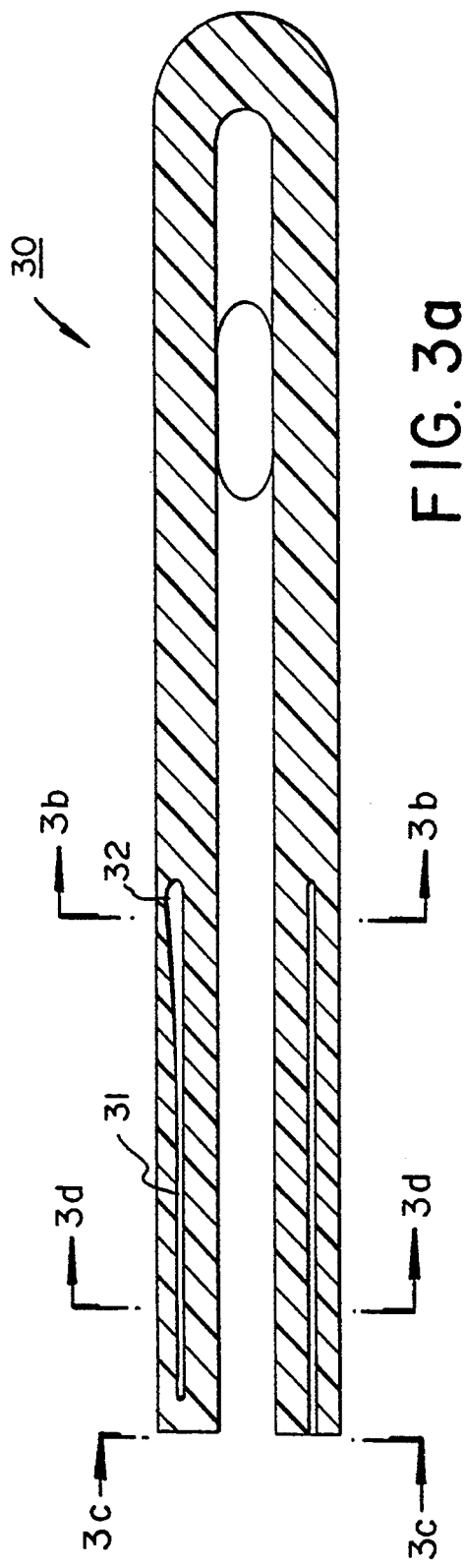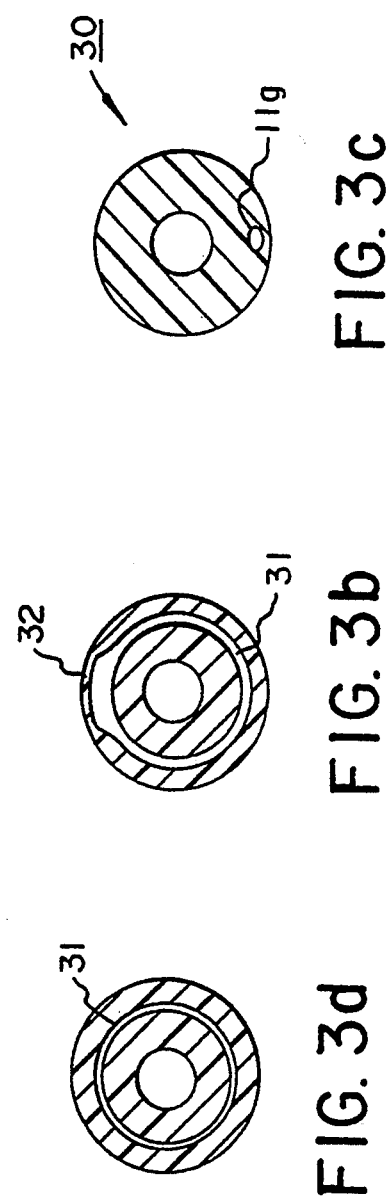

RUPTURABLE BALLOON SAFETY CATHETER

BACKGROUND OF THE INVENTION

This invention relates to catheterization and more particularly, to catheterization in which the possibility of internal injury to the patient is mitigated or avoided.

A catheter is a tubular instrument that is inserted into a passageway for a wide variety of actual and potential uses. One such use is the drainage of urine when natural discharge is impeded or prevented. Another use, provided by, the Eustachian catheter, entry to the middle ear for inspection or medical prosthesis.

Catheters are typically designed with a special tip that is inserted into a body cavity, such as the bladder. The tip communicates with an external end of the catheter tube through a hollow, elongated interior. This allows such functions as drainage, removal or inspection. For urine drainage, the most commonly used tube is the Foley cathether, named for its inventor.

In order to assure proper placement and retention of the catheter within the body, an annular, inflatable portion is spaced inwardly from the tip. The annular portion is normally deflated. It is inflated after insertion of the tip into the body, for example, the urinary bladder. The external end of the catheter also is provided with a branch arm by which the desired inflation can take place. For that purpose the branch arm includes a one-way valve through which fluid (water or air) can be admitted under pressure to the inflatable annular portion. This takes place through a narrow, elongated passageway extending substantially parallel to the main elongated and hollow cylindrical interior of the catheter tube.

By the introduction of either water or air under pressure into the branch arm, the annular portion of the catheter, when inflated, assumes a substantially toroidal shape. When a Foley catheter is inserted into the urinary bladder, the inflated annulus retains the tip of the catheter at the entrance of the bladder. This assures proper drainage through the opening provided in the catheter tip, and then through the hollow interior of the catheter to, for example, a waste container. Such a container may be strapped or otherwise affixed to the patient, typically at or above the knee.

The patient, or visitor, may accidentally step upon the waste container, or the waste container may become lodged or snagged, causing the Foley catheter to be pulled outwardly. In other cases the attendant removes the catheter by an excessive tug, or the patient withdraws it with a forceful tug.

With its toroidal portion fully inflated, the pulling or dislodging of a Foley catheter from the urinary bladder, and through the urethra, can cause severe lacerations and pain. In some cases there is severe bleeding and possible damage to the external urinary sphyncter, resulting in permanent urinary incontinence.

In other cases the catheter may be forcefully pulled from the patient because of a mistaken belief that the balloon of the catheter has been disinflated. Once again there is a possiblity of serious injury to the patient.

In an attempt to alleviate the damage that can be caused by premature catheter removal, the prior art of U.S. Pat. No. 3,951,153 provides a coupler for Foley catheters.

The coupler is positioned at an external location intermediate the ends of the catheter. It is adapted to enable a section of the catheter to become relatively easily and rapidly disconnected from the section of the catheter with the inflated balloon within the urinary bladder.

This disconnection is supposed to occur if the section of the catheter joined to the waste container is either accidentally or deliberately displaced from the remaining section. The disconnection is to prevent the remaining section from being drawn out of the urinary bladder to avoid laceration of the urinary canal, severe bleeding, possible urinary incontinence, and attendant pain.

The coupler of U.S. Pat. No. 3,951,153 is a circular shaped flange which is notched to anchor strips the severed end of the catheter, with the insertable tip firmly positioned, to form a water or air-tight seal for the passageway leading to the inflated toroid of the catheter. This allows the torroid to remain in its inflated position. The portion of the catheter joined to the waste container is force fitted on an oppositely directed, hollow cylindrical projection. This enables the section of the catheter joined to the waste container to be released from the coupler if either an accidental or deliberate force pulls this portion of the Foley catheter away. The portion inserted into the urinary bladder remains in position, preventing lacerations of the urinary canal, and such severe complications as bleeding and permanent urinary incontinence.

Unfortunately, the separate portions of the catheter in accordance with U.S. Pat. No. 3,951,153 do not always release as intended. In addition, there is the need for a special coupler, and the futher need to sever and slit the severed ends of the catheter.

It is therefore an object of the invention to provide for catheterization that facilitates catheter release when a pull is entered upon an inserted catheter with an inflated balloon. A related object is to prevent disastrous lacerations of the urinary canal. Another related object is to maintain a tight seal for the passageway used to inflate the inflatable portion.

Another object is to achieve release in the event that the portion of the catheter joined to a waste container is either deliberately or accidentally disturbed.

A further object of the invention is to overcome the shortcomings associated with U.S. Pat. No. 3,951,153, since the portions of the catheter in accordance with that patent do not always release as intended. A related object is to avoid the complication of requiring a special coupler, and the futher complication of the need to sever and slit one of the severed ends of the catheter.

SUMMARY OF THE INVENTION

In accomplishing the foregoing and related objects, the invention provides for insertion into a passageway of an elongated hollow member. Spaced from one end of the member is an inflatable portion with a weakened region. That portion is inflated after the member has been inserted into the passageway. The weakened region releases the inflation when the member is pulled from its inserted position.

In accordance with one aspect of the invention, the inflatable portion surrounds the member with a non-uniform thickness that forms the weakened region. The non-uniform thickness can extend over a part of the inflatable portion. The inflatable portion also can include a depression, and be oval, round, pointed and asymmetric.

A catheter in accordance with the invention has a slender, elongated and hollow tube with opposite ends.

One end is a tip adapted for insertion into a body cavity. The tip can have a pair of elongated openings that are diametrically opposed in a substantially cylindrical surface. The other end is adapted for connecting the hollow internal passageway as an inlet or outlet. The inflatable portion is spaced inwardly from the tip as a thin stretchable cylinder with a weakened region.

The tube can be used for distending a passageway or drawing fluid, especially distending the urinary passage or drawing urine from the bladder. The inflatable portion can be joined to a supplemental passageway extending to a branch tube. The latter is provided at its free end with a one-way valve structure that can be coupled to a source for introducing water or air under pressure to inflate the inflatable portion.

Another catheter in accordance with the invention is provided by a a slender elongated hollow tube with insert and access ends. The tube is adapted for insertion into a body cavity or passageway to distend the passage or draw fluid. The insert end of the tube has an opening to provide communication with the cavity. The access end, in turn, provides communication with the insert end, and the inflatable portion is spaced inwardly from the tip as a thin stretchable membrane with a weakened region. An auxilliary passage is provided for inflation.

In a method of producing apparatus for insertion into a passageway, the steps include (1) providing an elongated hollow member with opposite ends and (2) spacing, from one of the ends, an inflatable portion with a weakened region. Consequently, the weakened region of the inflatable portion releases the inflation when the member is pulled from its inflation position.

The method can include the step of surrounding the member with a non-uniform thickness to provide the weakened region. The non-uniform thickness can extend over a portion of the inflatable portion, which can include a round, oval shaped, pointed and asymmetric depression.

In a method of using an elongated hollow member in conjunction with a passageway, the steps include (1) inserting into the passageway the member with, an inflatable portion having a weakened region spaced from one end and (2) inflating the portion after the member has been inserted into the passageway. As a result the weakened region releases the inflation when the member is pulled from its inflation position.

The inflated portion can surround the member with a non-uniform thickness to provide the weakened region and extend over a portion of the inflated portion. When the member is pulled along the passageway, the weakness, coupled with the force of the pull, causes the inflated portion to release the liquid or air and collapse. Alternatively, when the member is pulled along the passageway, the weakened region can cause the inflated portion to rupture and permit the withdrawal of the member without injury. The member also can be used to provide access to a body cavity in order to permit inspection of the cavity or use of a medical instrument.

DESCRIPTION OF THE DRAWINGS

Other aspects of the invention will become apparent after consideration of several illustrative embodiments, taken in conjunction with the drawings, in which:

FIG. 1 is a perspective view of a Foley catheter in accordance with the prior art.

FIG. 1a is a sectional view of the catheter of FIG. 1 taken along the lines 1a–1a.

FIG. 2a is an illustration showing the catheter of FIG. 1 in use.

FIGS. 2b–2d are views of the catheter of FIG. 1 as modified in accordance with the prior art.

FIGS. 3a–3d show sectional views of a catheter modified in accordance with the invention.

DETAILED DESCRIPTION

Figure 4A:
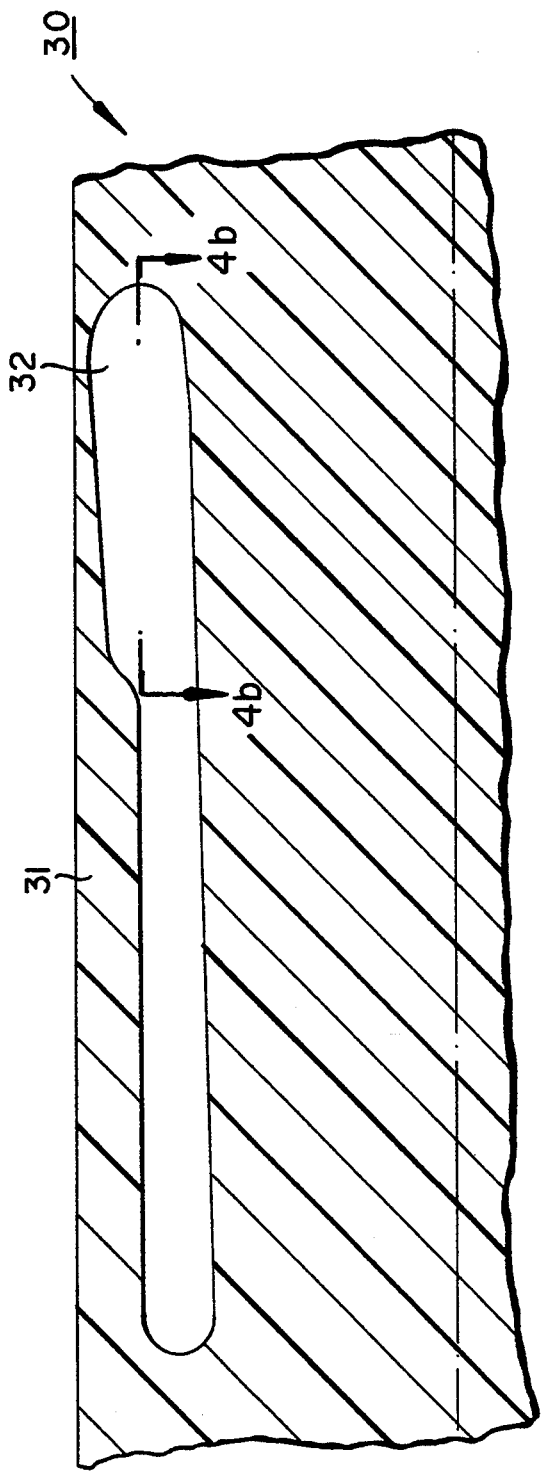
FIGS. 4a–4b are sectional views showing details of FIGS. 3a and 3b.

With reference to the drawings, FIGS. 1 and 1a show a Foley catheter 10 which is typically a slender elongated hollow tube 11 for insertion into a body cavity, to distend the passage or draw fluid. The Foley catheter is especially used for distending and/or drawing urine from the bladder.

The free end 11a of tube 11 has a pair of elongated openings 11b which are diametrically opposed about the substantially cylindrical surface of the tube 11 at its insertion end. The opposite end 11n is used for connecting a hollow internal passageway 11d in any appropriate manner, for example to a waste container.

Spaced inwardly from tip 11a is a thin stretchable cylindrical portion 11e, which is joined to hollow tubular branch portion 11f by which water or air can be applied to a passageway 11g, shown in FIG. 1a, extending from the inflatable portion 11e along the tube 11 and then along the branch tube 11f. The latter is provided at its free end with a one-way valve structure 11h that can be coupled to a source of water or air to be introduced under pressure through the one-way valve structure 11h.

In using the catheter 10, as shown in FIG. 2a, the tip 11a is inserted into a passageway 22a. Once the tip has reached a specified region, such as a urinary bladder 23a, the stretchable portion 11e is expanded by the application of air or water under pressure to the one-way valve 11h at the branch tube 11f. Typically, the injection is of air by using a syringe (not shown) which depresses the one-way valve 11h and allows air to enter the stretchable portion 11e, as a plunger of the syringe is depressed. The result is as indicated in FIG. 2b where the stretchable portion 11e has expanded to a balloon shape 11j. This secures the catheter 10 in a desired position within, for example, the urinary bladder 13a.

In the prior art, a splicing and coupling technique has been employed in an attempt to prevent damage to the passageway 22a and the cavity 23a, when the catheter 10 is forcefully removed with the balloon 11j inflated. The splicing and coupling technique requires that the catheter 10 be clamped as illustrated at position 25a and 25b in FIG. 2b, after which the catheter is severed and the ends of the catheter are applied to a coupler 22 as shown in FIGS. 2c and 2d.

As a preliminary procedure, the severed end of that part of the catheter that leads to the balloom 11j is spliced as shown in FIG. 2c in order to be secured to a coupler 22. The other severed end of the catheter 10 is seated on a cylindrical boss of the coupler 22 with the result depicted in FIG. 2d. With this arrangement, any action that brings about a pulling force on the catheter, is supposed to result in a decoupling at the coupler position. The purpose is to prevent the inflated balloon 11j from being pulled from the cavity 23a, and simultaneously allow deflation of the balloon 11j so that removal can take place safely.

Unfortunately, the coupling procedure illustrated in FIGS. 2b–2d requires severing of the catheter and splicing it. The typical catheter is made of an elastomeric polymer that resists splicing and slicing, so that it is difficult in practice to implement the prior art. In addition, the implementation is complex and time consuming, and the spliced ends do not always seat properly on the coupler, with the result of leakage that can cause premature deflation of the balloon 11j.

The invention overcomes the shortcomings and difficulties of the prior art. As illustrated in the cross-sectional view of FIG. 3a, for a catheter 30 in accordance with the invention, the stretchable portion 31 is provided with a weakened region 32 that is illustrated in detail in FIG. 4a.

Also shown are various cross-sections of the catheter 30 including a cross-section along the lines 3D—3D shown in detail in FIG. 3d; and the section along the lines 3B—3B including the weakened region 32, shown in FIG. 3b. Also shown is the cross section along the lines 3C—3C, shown in FIG. 3c.

With respect to the detailed view of FIG. 4a, the interval between the core of the catheter and the stretchable membrane 31 is enlarged to leave a thin, weakened region near the outer surface of the catheter. In an illustrative example of a catheter in accordance with the invention, the weakened region had a maximum thickness of 0.005 inch and extended for about 0.25 inch downwardly to a wall thickness of 0.015 inch.

Figure 4B:
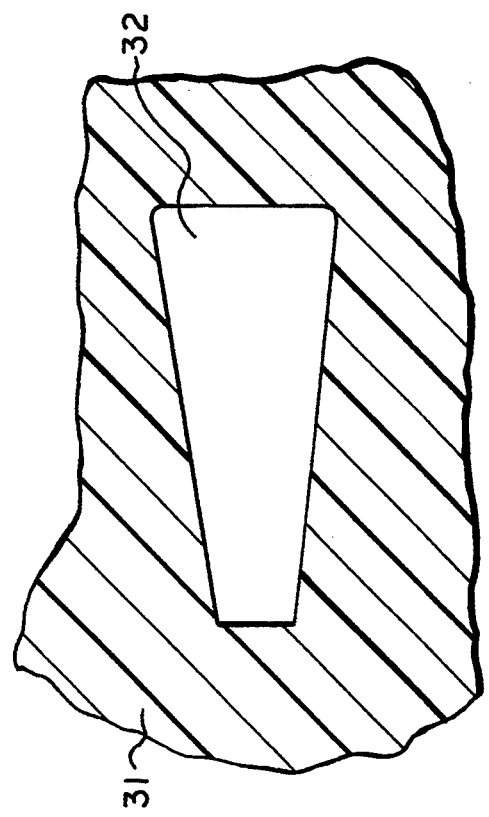

A sectional view with respect to the weakend region is shown along the lines 4A—4A and illustrated in FIG. 4b.

In the manufacture of a catheter in accordance with the invention having weakened region in the inflatable portion, the part of the catheter extending to the weakened region is formed in conventional fashion to the break line BR—BR in FIGS. 4a and 4b. The remaining part is then formed in conventional fashion, and the two parts are joined, for example, by ultrasonic welding.

It will be understood that the foregoing detailed description is for illustration only and that other modifications, adaptations, uses and procedures in accordance with the invention will be readily apparent to persons of ordinary skill in the art.

What is claimed:

1. Apparatus for insertion into a passageway, comprising
    an elongated hollow member having opposite ends;
    said member having, spaced from one end, an inflatable portion with a weakened region; and
    means for inflating said portion after said member has been inserted into said passageway;
    whereby the weakened region of said inflatable portion releases the inflation of said portion when said member is pulled from its inflation position; wherein said inflatable portion surrounds said member with a non-uniform thickness to provide said weakened region.

2. Apparatus as defined in claim 1 wherein said non-uniform thickness extends partially over said inflatable portion.

3. Apparatus as defined in claim 2 wherein said inflatable portion includes a depression therein.

4. Apparatus as defined in claim 3 wherein said depression is round, pointed or oval shaped.

5. Apparatus as defined in claim 4 wherein said oval shaped depression is asymmetric.

6. Apparatus as defined in claim 1 comprising a catheter wherein said member is a slender, elongated hollow tube having opposite ends;
    one of said ends is a tip for insertion into a body cavity and provided with a pair of elongated openings diametrically opposed about a substantially cylindrical surface;
    the other of said ends is for connecting the hollow internal passageway as an inlet or outlet; and
    said inflatable portion is spaced inwardly from said tip as a thin stretchable cylinder with a weakened region.

7. Apparatus as defined in claim 6 wherein said tube comprises means for distending said passageway or drawing fluid there along, including distending the urinary passage or drawing urine from the bladder to a waste container.

8. Apparatus as defined in claim 6 wherein said inflatable portion is joined to a supplemental passage extending to a branch tube provided with a one-way valve structure for coupling to a source for introducing water or air under pressure through said one-way valve structure for inflating said portion.

9. A catheter as defined in claim 1 comprising
    a slender elongated hollow tube having insert and access ends;
    said tube being insertable into a body cavity to distending the passageway or drawing fluid;
    the insert end of said tube being provided with an opening to communicate with said cavity;
    said access end being adapted for providing communication with said insert end; and
    said inflatable portion being spaced inwardly from said tip with a weakened region joined to means for inflating said portion.

10. The method of providing apparatus for insertion into a passageway, comprising the steps of:
    (1) providing an elongated hollow member having opposite ends; and
    (2) spacing, from one end of said member, an inflatable portion with a weakened region;
    whereby the weakened region of said inflatable portion releases the inflation of said portion when said member is pulled from its inflation position; including the step of surrounding said member with a non-uniform thickness to provide said weakened region.

11. The method of claim 10 wherein said non-uniform thickness extends partially over a portion of said inflatable portion.

12. The method of claim 11 wherein said inflatable portion includes a depression therein.

13. The method of claim 12 wherein said depression is round, pointed or oval shaped and asymmetric.

14. The method of using an elongated, oppositely-ended hollow member in conjunction with a passageway, comprising the steps of:
    (1) inserting into said passageway one end of said member having, spaced therefrom, an inflatable portion with a weakened region; and
    (2) inflating said portion after said member has been inserted into said passageway;
    whereby the weakened region of said inflatable portion releases the inflation of said portion when force is applied to pull said member from its inflation position;
    wherein the inflated portion surrounds said member with a non-uniform thickness providing said weakened region and extending partially over a portion of said inflated portion.

15. The method of claim 14 wherein said member is pulled along said passageway to cause said inflated portion to collapse.

16. The method of claim 14 wherein said member is pulled along said passageway to cause said inflated portion to rupture and permit the withdrawal of said member without injury.

17. The method of claim 14 wherein said member is used to provide access to a body cavity to permit inspection of the cavity or use of a medical instrument therein.

* * * * *